United States Patent [19]
Latterell et al.

[11] Patent Number: 5,300,110
[45] Date of Patent: Apr. 5, 1994

[54] DIRK-BASED EPICARDIAL DEFIBRILLATION ELECTRODE

[75] Inventors: Scott T. Latterell, Minneapolis; Mark W. Kroll, Minnetonka; Theodore P. Adams, Edina, all of Minn.

[73] Assignee: Angeion Corporation, Plymouth, Minn.

[21] Appl. No.: 961,463

[22] Filed: Oct. 15, 1992

[51] Int. Cl.⁵ ............................................. A61N 1/04
[52] U.S. Cl. .................................................. 607/130
[58] Field of Search ............... 128/642, 785, 784, 639

[56] References Cited

U.S. PATENT DOCUMENTS

| | | | |
|---|---|---|---|
| 4,030,509 | 6/1977 | Heilman et al. | 128/419 |
| 4,058,128 | 11/1977 | Frank et al. | 128/785 |
| 4,066,085 | 1/1978 | Hess | 128/785 |
| 4,291,707 | 9/1981 | Heilman et al. | 128/784 |
| 4,355,642 | 10/1982 | Alferness | 128/642 |
| 4,817,634 | 4/1989 | Holleman et al. | 128/784 |
| 4,827,932 | 5/1989 | Ideker et al. | 128/419 |

Primary Examiner—William E. Kamm
Assistant Examiner—Scott M. Getzow
Attorney, Agent, or Firm—Anthony G. Eggink

[57] ABSTRACT

An epicardial defibrillation electrode device having small conductive dirks extending therefrom to lodge into the myocardium to lower the electrode impedence. The electrode device utilizes a flexible, translucent support member to aid in the positioning of the dirks during electrode implantation. Switchable dirks extending from separate conductive members mounted to the support member are provided for pacing, sensing and defibrillation.

20 Claims, 3 Drawing Sheets

DIRK-BASED EPICARDIAL DEFIBRILLATION ELECTRODE

BACKGROUND OF THE INVENTION

The invention relates generally to defibrillation electrodes and particularly to epicardial defibrillation electrodes having conductive dirk members to penetrate the epicardium.

To perform defibrillation with the voltages and energies that are available from present implantable devices it is critical that the resistance of the defibrillation electrodes be as low as possible. Although various types and configurations of electrodes have been proposed and used for defibrillation, epicardial patch electrodes continue to be the most effective defibrillation electrode structures. However, a shortcoming of the epicardial patch is that a large portion of the voltage may not effectively penetrate into the myocardium. For example, animal studies have shown that up to 70% of the electrode potential is lost in the first few millimeters of the heart.

One prior art approach at lowering the electrode impedance is the use of relatively large electrode structures which are contoured to the shape of the heart and stitched in place. A drawback of these structures is that with sufficiently large patches they may be positioned too close to each other. As a result, the defibrillation current may take the shortest route from the edge of one patch to that of the adjacent patch causing the beneficial defibrillation current to the heart to be shunted away.

Although various epicardial defibrillation electrode configurations have been utilized and proposed, they have generally been designed to be positioned against the epicardium or to be implanted subcutaneously a distance from the heart. The object of the present invention is to provide an epicardial defibrillation electrode having outwardly extending dirks which penetrate the epicardium and contact the myocardium.

A further object is to provide dirk based epicardial electrode devices which utilize support members which aid in the positioning and implantation of the electrodes. Another object of the invention is to provide epicardial electrode devices having a plurality of outwardly extending dirk members and circuitry in communication therewith and which may be utilized for pacing, sensing and defibrillation.

SUMMARY OF THE INVENTION

The present invention provides an epicardial patch electrode which penetrates the epicardium. The electrode comprises a support structure having an elongated conductor to which a plurality of outwardly extending dirks are attached. The dirk-based epicardial defibrillator electrodes comprise electrode structures which utilize flexible membranes which support various configurations of dirk-based defibrillation conductors which are adjustably implantable at specified epicardial positions. The dirk members extend outwardly from the flexible support structure and have terminal barbs for penetrating and lodging into the myocardium.

The dirk based epicardial electrode devices further provide electrode structures constructed of materials and arranged to aid in the conforming positioning of the electrodes to contact the myocardium. Other electrode embodiments are provided having a plurality of dirk members connected to separate conductive members mounted to the support structure which may be utilized for pacing, sensing and defibrillation.

These and other benefits of this invention will become clear from the following description by reference to the drawings.

DESCRIPTION OF THE PREFERRED EMBODIMENTS

Figure 1:
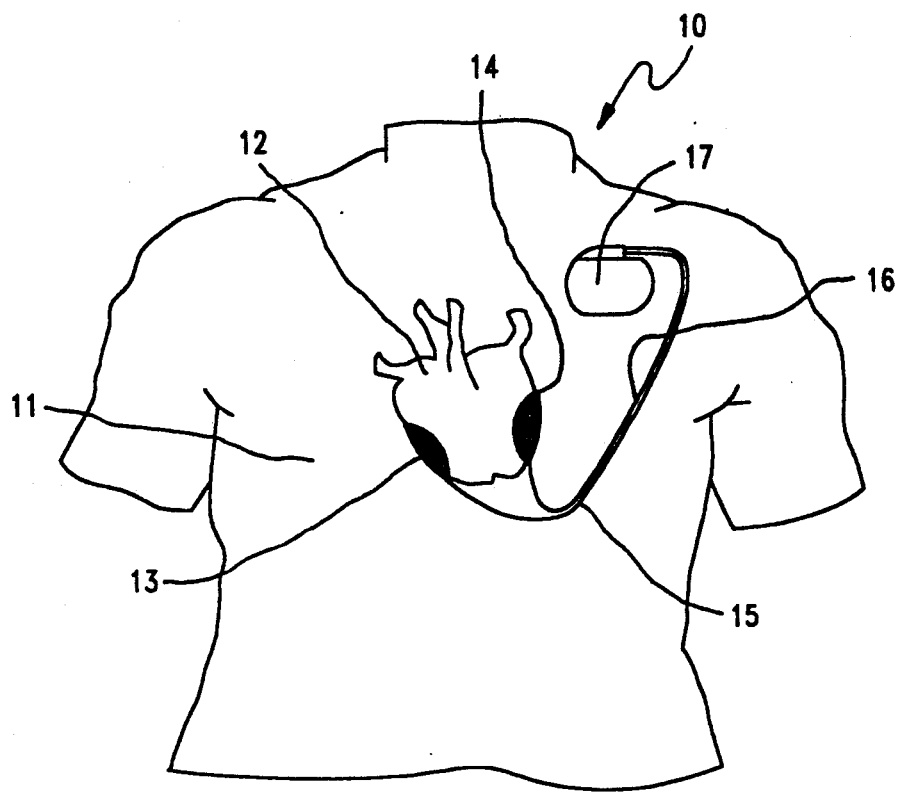
FIG. 1 is a plan view showing a pair of epicardial defibrillation patch electrodes positioned on the heart and connected to an implanted cardioverter defibrillator housing.
Figure 2:
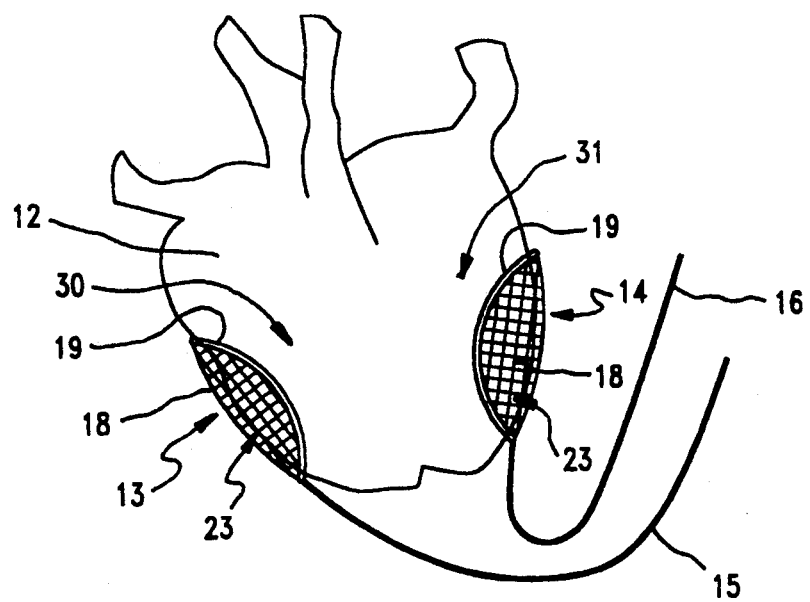
FIG. 2 is a plan view further showing patch electrodes epicardially positioned on the heart.

As background information, FIG. 1 shows a pair of epicardial patches 13 and 14 positioned on the heart 12 and connected to an implantable cardioverter defibrillator or ICD 17. As shown, the chest area 11 of a patient 10 has the patch electrodes 13 and 14 epicardially positioned about heart 12 and respectively connected via electrode leads 15 and 16 to a defibrillator pulse generator 17 positioned in the pectoral region. FIG. 2 further shows the patch electrodes 13 and 14 positioned at the right and left ventricle surfaces 30 and 31, respectively, of the heart 12. The patch electrodes are typically placed adjacent the epicardium of the heart or implanted subcutaneously a specified distance from the heart. Patch electrode structures generally have areas ranging from ten to thirty square centimeters or more and have mesh structure 23 comprised of flexible conductive netting 18 which is generally woven and which may or may not be supported by a nonconductive member.

The typical epicardial patch electrode presently used resembles a rectilinear structure having an elongated lead attached to a woven screen of metal. Alternative configurations utilize knitted materials as disclosed in Applicant's assignee's application Ser. No. 886,784 to Gilman et al. Prior art epicardial patches are typically implanted adjacent the heart and do not penetrate the epicardium. These electrode devices are thin and relatively flat structures and, as discussed above, have a relatively high impedance.

Figure 3:
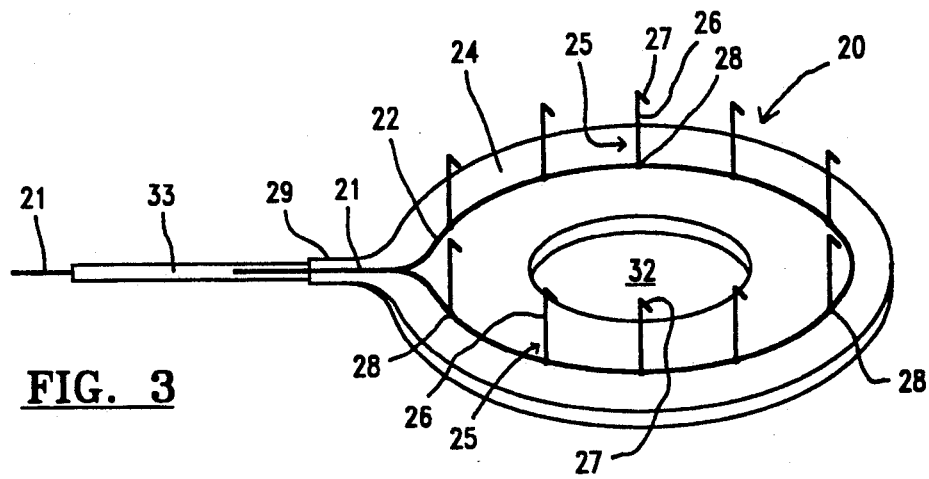
FIG. 3 is an isometric top plan view of the dirk-based epicardial defibrillation patch electrode device of the present invention.

FIG. 3 shows the basic structure of this invention wherein the dirk-based electrode device 20 is shown to have a connecting lead 21 with an insulated covering 33 which extends to the base 29 of support structure 24. Imbedded in or mounted to the support structure 24 is a defibrillation current conducting ring 22. Importantly, a plurality of dirk members 25 are connected to the conducting ring 22 at connection points 28. As shown, each dirk member 25 has an elongated body 26 having a terminal barb 27 which serves as a means to anchor the dirks in the myocardium.

Figure 6:
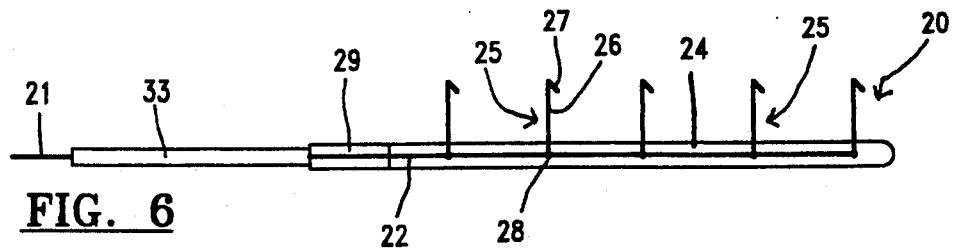
FIG. 6 is a cross-sectional view of the dirk-based epicardial patch electrode of FIG. 3.

As further shown in the crossectional view of FIG. 6, the epicardial patch 20 has a number of dirks 25 projecting upwardly in a perpendicular direction relative to the support structure 24. Each dirk member 25 preferably has a length of between 1-10 mm. These dirk member lengths are suitable for epicardial implantation at the right and left ventricle regions of the heart. However, since the left ventricle has more thickness than the right ventricle, longer dirks could be utilized in a left ventricular patch. The dirks 25 are electrically connected to the common current carrier 22 which is held in or on the substrate 24 of the electrode. As shown, each dirk 25 has a small barb 27 attached at its terminal end which maintains the electrode in position with respect to the heart after implantation. The dirk members 25 may be provided with terminal barbs 27 for anchoring in the myocardium. However, because the flexible support 24 may be stitched to the epicardium of the heart, a dirk barb 27 may or may not be necessary. Thus, depending upon the nature of the physical securement by the physician of the dirk based electrode structure to the epicardium, the terminal barbs 27 on the dirk members 25 may not be required.

A centrally positioned cut out 32 is shown in the donut or disc shaped electrode body 24 which is preferably formed of a flexible polymer substrate which is transparent or translucent. Suitable substrates for the support structure 24 include silicone rubber and polyurethane compounds and like biocompatable materials. The central aperture 32 provides flexibility to the electrode support body 24 which permits flexible conformance to the epicardium for implantation purposes and which also provides flexibility to yield lower physical impedence for heart movement subsequent to implantation.

The support substrate 24 is preferably transparent or translucent so that the physician is able to see precisely where each dirk 25 will penetrate the epicardium and the myocardium during implantation. This is important so that the electrode patch 20 can be placed in such a position where none of the dirks 25 damage the heart, such as the coronary arteries. The physician, therefore, may snap off or otherwise remove any dirk 25 that could possibly interfere or cause damage. Optionally, the base of each dirk member may be indented or notched to provide means for the easy removal of any individual dirk member.

A primary advantage of the dirk based electrode structures of this invention, is that defibrillation can be accomplished with much lower voltages and energies. This is due primarily to two factors. First, the impedance of the dirk based electrode 20 is lower and therefore less voltage is needed to drive the same current through the heart. Second, the dirks 25 will deliver the current deeper into the heart so that there is less loss in the outer millimeters in the myocardium. In summary, because less current is required for defibrillation, the dirk based electrodes are more effective and cause less damage to the heart.

Another benefit of this invention is that, for the same defibrillation threshold, the electrode can be made much smaller. As is known, large patch electrodes can be difficult to contour and attach to the heart. There is also evidence that large electrodes may interfere with the physical movement of the heart and have been shown to abrade through coronary arteries, for example. The dirk based epicardial electrodes of this invention allow defibrillation with much lower energies for the same electrode surface area and therefore a specified threshold can be attained with a smaller electrode.

A further benefit of the dirk based electrodes of this invention is that one or two of the dirks may be individually or separately wired. Such an electrode configuration allows those particular dirks to be used for pacing and sensing of the heart's rhythm. Circuitry in the cardioverter defibrillator could, optionally, use those same two dirks, for example, also for defibrillation purposes when required. This type of circuitry could also be built into the patch itself. Thus, the electronic circuitry can be used to separate pacing and sensing functions from the defibrillation current while eliminating one or two of the additional conductors that are typically required.

Figure 4:
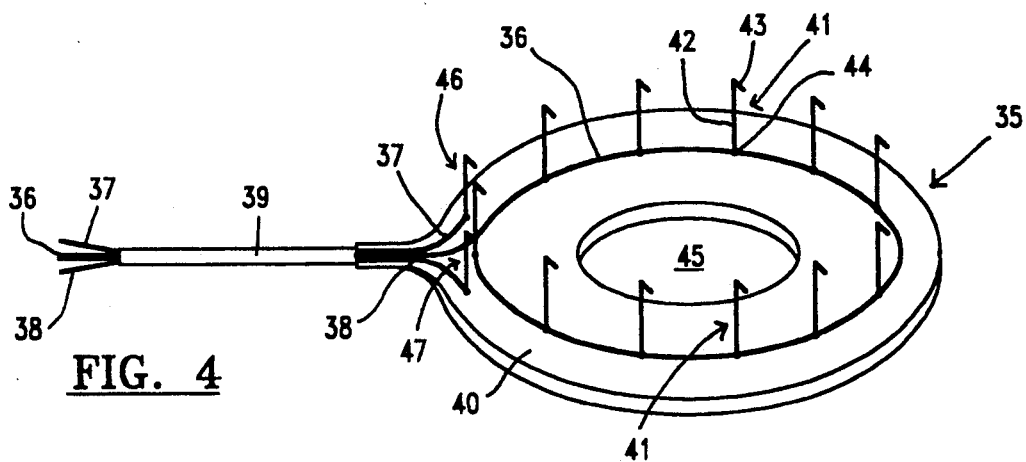
FIG. 4 is an isometric top plan view of another dirk-based epicardial defibrillation patch electrode device embodiment.

In view of the above, FIG. 4 shows an electrode embodiment 35 having two separate pacing and sensing dirks 46 and 47, each having separate conductors 37 and 38. A high current conductor ring 36 is shown mounted to support structure 40 for the dirk members 41 that are designed to carry the defibrillation current. A central cut out 45 is further shown in the flexible support structure 40. The pacing/sensing conductor leads 37 and 38 are show to extend from the insulated conductor structure 39 to the support structure 40 from which extend the pacing/sensing dirk members 46 and 47 and the defibrillation dirk members 41.

Figure 5:
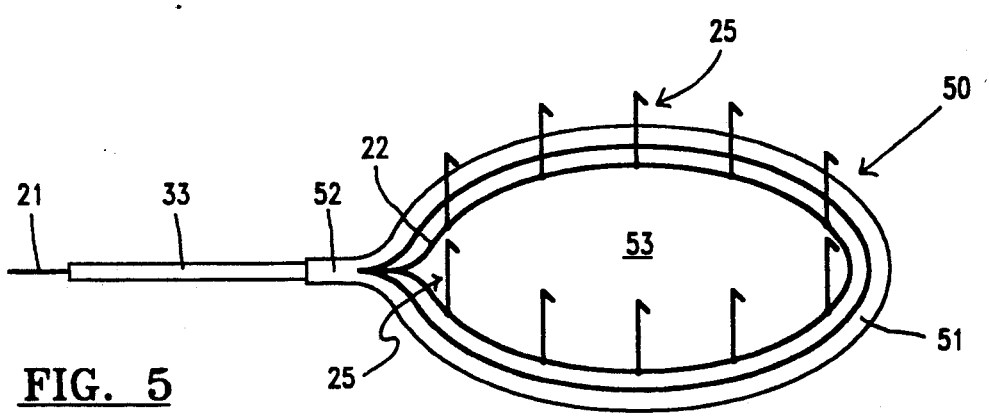
FIG. 5 is an isometric top plan view of another dirk-based defibrillation patch electrode embodiment.
Figure 7:
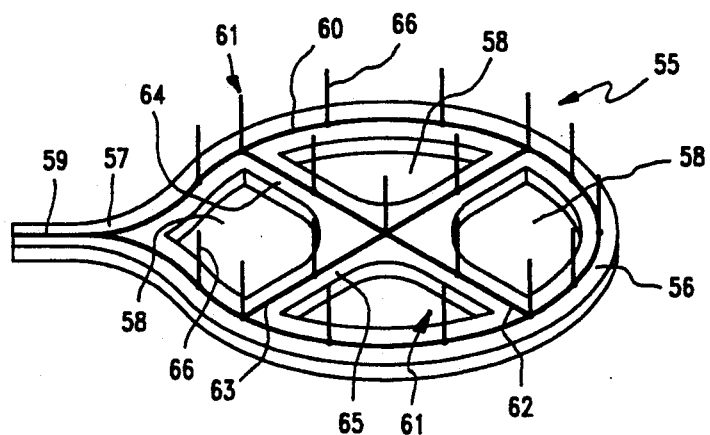
FIG. 7 is an isometric top plan view of another dirk-based patch electrode embodiment.

FIG. 5 shows a dirk-based electrode embodiment 50 wherein a support membrane 53 is attached to a peripheral frame structure 51. As described with respect to the embodiment 20 of FIGS. 3 and 6, the connecting lead 21 enters the frame base 52 to form a defibrillation current conducting ring 22 having a plurality of dirk members 25 connected thereto and extending outwardly from the support membrane 53. As measured with respect to the outer perimeter of the electrode device, and including the cut out or cut outs of the support membranes, the electrodes of the present invention may have areas varying from ten to forty square centimeters FIG. 7 shows a dirk based electrode embodiment 55 wherein a frame structure 56 having a base 57 is utilized to support a current conducting ring 60 which is connected to the defibrillation current lead 59. Frame cross members 64 and 65 are shown extending between the peripheral portion of the frame 56 and defining open areas or apertures 58. Current conducting segments 62 and 63 are mounted on or in the cross members 64 and 65, respectively, and connected to the current conducting ring 60. A plurality of dirk members 61 are shown connected to and extending outwardly from the conducting ring 60 and the conducting segments 62 and 63. The dirk bodies 66 are elongated conductive members which have a generally uniform diameter along their lengths. Unlike the previously described dirk members, the dirk members 61 do not have terminal barbs. The frame structure of embodiment 55 is preferably a flexible, biocompatable structure which can be positioned in a contoured configuration with respect to the heart and which flexes with the heart movement after implantation. The open areas 58 further aid in the initial positioning of the electrode embodiment 55 and the frame cross members 64 and 65 provide a supporting structure for the interconnected conducting segments 62 and 63 and the associated dirk members 61 to yield a greater area for defibrillation.

Figures 8, 9, 10:
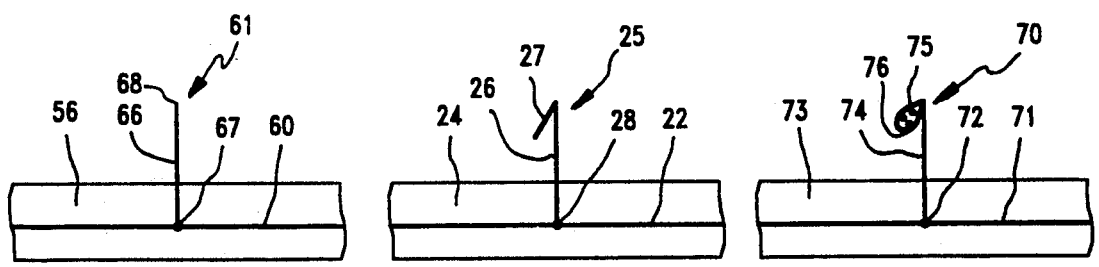
FIGS. 8-10 are lateral plan views showing dirk members utilized in the electrode embodiments of the present invention.

FIGS. 8, 9 and 10 show several dirk member embodiments which may be utilized in the epicardial defibrillation electrodes of the invention. The dirk member 61 of FIG. 8, and also shown in FIG. 7, is connected at 67 to the conductor 60 in frame support 56. The dirk member 61 has an elongated body 66 having a terminal end 68. The dirk member 25 of FIG. 9, and also shown in FIG. 3, is connected at 28 to conductor 22 in support structure 24. The dirk member 25 has an elongated body 26 having a terminal barb 27. The terminal barb 27 serves as an anchoring means for the dirk member and although one such barb is shown, additional barbs may be added. Further, other anchoring means may be utilized with the dirk members of this invention. For example, FIG. 10 shows a dirk member 70 connected at 72 to conductor 71 in support structure 73. The dirk member 70 has an elongated body 74 having a terminal plate-like member 75 with apertures 76. Subsequent implantation, soar tissue will form through the apertures 76 to further anchor the dirk in the myocardium. Thus, various anchoring means may be utilized with the dirks to firmly position them in the myocardium.

In summary, the dirk based electrodes of the invention may be constructed of a flexible support structure having a thickness wherein a peripheral frame is not required as shown in FIGS. 3, 4 and 7. Alternatively, a thinner support membrane 53 may be utilized, as shown in FIG. 5, wherein a peripheral frame structure 51 is utilized. In both configurations, the defibrillation current conductors are mounted to or imbedded in the respective support substrates whereby the dirk members extend outwardly therefrom. Further, centrally disposed apertures in the respective support substrates may be provided interiorly to the supported conductors to give further flexibility to the electrode for implantation purposes as well as to minimize the physical impedance of the implanted electrode on the heart.

As many changes are possible to the embodiments of this invention utilizing the teachings thereof, the descriptions above, and the accompanying drawings should be interpreted in the illustrative and not the limited sense.

That which is claimed is:

1. An epicardial defibrillation electrode comprising a flexible base member having a peripheral edge, a conductive member supported by said base member and extending inward from and adjacent said peripheral edge, said conductive member having a plurality of outwardly extending and generally parallel dirk members connected thereto, each said dirk member further having a terminal end portion constructed and arranged for penetrating the myocardium and for delivering a defibrillation current.

2. The epicardial defibrillation electrode of claim 1, wherein each said dirk member has an elongated conductive body member having anchoring means at said end portion.

3. The epicardial defibrillation electrode of claim 2, wherein said anchoring means is comprised of a barbed structure.

4. The epicardial defibrillation electrode of claim 2, wherein said anchoring means is comprised of a plate member having at least one aperture therethrough.

5. The epicardial defibrillation electrode of claim 1, further comprising a deformable peripheral frame structure for supporting said flexible base and wherein said flexible base is comprised of a translucent material.

6. The epicardial defibrillation electrode of claim 1, further comprising at least one second conductive member supported by said base member, said at least one second conductive member having an outwardly extending second dirk member for penetrating the myocardium, said at least one second conductive member further being connected to pacing/sensing means.

7. The epicardial defibrillation electrode of claim 1, wherein each said dirk member has a length of between 1 to 10 mm.

8. The epicardial defibrillation electrode of claim 1, wherein said flexible base member has at least one aperture therethrough.

9. An epicardial defibrillation electrode device for use in a defibrillator assembly comprising:
   a) a support base structure constructed of a flexible, translucent and biocompatable plastic material;
   b) at least one elongated curvilinear conductive member supported by said base structure; and
   c) at least one outwardly extending dirk member connected to said conductive member.

10. The epicardial defibrillation electrode device of claim 9, wherein said at least one dirk member has a length between 1 to 10 mm and has anchoring means connected thereto.

11. The epicardial defibrillation electrode device of claim 9, wherein at least one second conductive member is supported by said support base structure and connected to pacing/sensing means and wherein a second dirk member extends outwardly from said second conductive member.

12. The epicardial defibrillation electrode device of claim 9, wherein said conductive member and said at least one dirk member is comprised of a conductive material selected from the group of materials comprising stainless steel, titanium, platinum, nickel/chromium alloys and silver composites.

13. The epicardial defibrillation electrode device of claim 12, wherein said support base structure has at least one aperture therethrough.

14. The epicardial defibrillation electrode device of claim 9, wherein said support base structure has a frame structure peripherally attached thereto, said frame structure being comprised of a conforming structure.

15. An implantable defibrillation electrode device for use in a defibrillator assembly comprising:
   a) a conformable frame structure forming a generally closed peripheral support structure terminating at a base;
   b) a flexible support material spanning and being connected to said frame structure;
   c) at least one elongated conductive member supported by said support material;
   d) a plurality of outwardly extending dirk members connected to said at least one elongated conductive member, said dirk members being arranged about the periphery of said flexible support material and forming a loop thereabout; and
   e) conductive lead means being in electrical communication with said at least one conductive member.

16. The epicardial defibrillation electrode of claim 15, wherein each said dirk member has an elongated body member having anchoring means connected thereto.

17. The epicardial defibrillation device of claim 15, wherein each said conductive member and said dirk member are comprised of a material selected from the group of materials of stainless steel, titanium, platinum and silver alloys.

18. An implantable electrode device for the conforming placement at epicardial positions comprising a flexible patch structure of a predetermined configuration having a flexible and conforming frame structure comprising a non-conductive support material, an elongated conductive member supported by said support material and having a plurality of outwardly extending and generally parallel dirk members, and means to electrically connect said patch structure to a conductive lead, each said dirk member extending generally at a right angle from said support material and having an elongated body with a terminal end constructed and arranged to penetrate the myocardium and to deliver a defibrillation current.

19. The electrode device of claim 18, wherein each said dirk member has an elongated conductive body member having anchoring means.

20. The electrode device of claim 18, wherein said elongated conductive member and said dirk members are constructed of a material selected from the group of materials comprising stainless steel, titanium, platinum, nickel/chromium alloys and silver composites.

* * * * *